(12) United States Patent
De Ruijter et al.

(10) Patent No.: US 8,646,591 B2
(45) Date of Patent: Feb. 11, 2014

(54) APPARATUS FOR HANDLING CAPSULES AND CAPSULE PROCESSING EQUIPMENT INCLUDING SUCH AN APPARATUS

(75) Inventors: Thomas Marcelina Louis De Ruijter, Bornem (BE); Nigel David Harrison, Melbourn (GB); Martin Lawrence Hughes, Melbourn (GB); Mark Robson Humphries, Melbourn (GB); Paul Antony Merritt, Melbourn (GB); Stefaan Jaak Vanquickenborne, Bornem (BE); Philip Jonathan West, Melbourn (GB)

(73) Assignee: Capsugel Belgium NV, Bornem (BE)

(*) Notice: Subject to any disclaimer, the term of this patent is extended or adjusted under 35 U.S.C. 154(b) by 343 days.

(21) Appl. No.: 13/130,322

(22) PCT Filed: Nov. 5, 2009

(86) PCT No.: PCT/IB2009/054917
§ 371 (c)(1),
(2), (4) Date: May 20, 2011

(87) PCT Pub. No.: WO2010/058312
PCT Pub. Date: May 27, 2010

(65) Prior Publication Data
US 2011/0222993 A1    Sep. 15, 2011

Related U.S. Application Data

(60) Provisional application No. 61/116,466, filed on Nov. 20, 2008.

(51) Int. Cl.
*A61J 3/00* (2006.01)
*A61J 3/07* (2006.01)

(52) U.S. Cl.
USPC ........................................... 198/397.01

(58) Field of Classification Search
USPC ................. 198/393, 394, 395, 396, 397.01, 198/803.14, 867.11; 209/576, 577, 686
See application file for complete search history.

(56) References Cited

U.S. PATENT DOCUMENTS

| | | | |
|---|---|---|---|
| 2,771,191 A | 11/1956 | Kath | 209/75 |
| 3,756,402 A | 9/1973 | Wagers et al. | 209/73 |
| 3,838,766 A | 10/1974 | Wagers, Jr. et al. | |
| 4,437,559 A * | 3/1984 | Ackley et al. | 198/397.04 |
| 4,582,201 A * | 4/1986 | Taniguchi et al. | 209/587 |
| 5,085,510 A | 2/1992 | Mitchell | 356/237 |
| 5,836,243 A | 11/1998 | Ackley | 101/44 |
| 6,079,284 A * | 6/2000 | Yamamoto et al. | 73/865.8 |
| 7,456,946 B2 * | 11/2008 | Ackley et al. | 356/237.1 |
| 7,701,568 B2 * | 4/2010 | Ackley et al. | 356/237.1 |
| 8,091,319 B2 * | 1/2012 | Ream et al. | 53/111 R |

(Continued)

OTHER PUBLICATIONS

PCT/IB2009/054917 (WO 2010/058312), Written Opinion of the International Searching Authority, dated Feb. 10, 2010, 6 pages.

(Continued)

*Primary Examiner* — Douglas Hess
(74) *Attorney, Agent, or Firm* — Finnegan, Henderson, Farabow, Garrett & Dunner, LLP

(57) ABSTRACT

The invention relates to an apparatus for handling capsules in a capsule processing equipment. The invention also relates to capsule processing equipment, such as an inspection equipment or a capsule printing equipment that includes such an apparatus.

14 Claims, 5 Drawing Sheets

(56) References Cited

U.S. PATENT DOCUMENTS

| | | |
|---|---|---|
| 8,141,697 B2 * | 3/2012 | Ackley, Jr. .............. 198/803.14 |
| 8,220,619 B2 * | 7/2012 | Ackley .................... 198/803.13 |
| 8,269,958 B2 * | 9/2012 | Ackley et al. ............. 356/237.1 |
| 2004/0094389 A1 | 5/2004 | Boyce |

OTHER PUBLICATIONS

PCT/IB2009/054917 (WO 2010/058312), Internationals Search Report, dated Feb. 10, 2010, 7 pages.

* cited by examiner

APPARATUS FOR HANDLING CAPSULES AND CAPSULE PROCESSING EQUIPMENT INCLUDING SUCH AN APPARATUS

This application is a National Stage filing of PCT/IB2009/054917 filed Nov. 5, 2009, which claims priority to U.S. Provisional Patent Application No. 61/116,466 filed Nov. 20, 2008, the disclosures of which are hereby incorporated by reference in their entirety.

The invention relates to an apparatus for handling capsules in a capsule processing equipment, such as an in-line inspection equipment or an in-line printing equipment for processing capsules of a type used in the pharmaceutical industry and/or dietary supplement industry.

More specifically, the invention is intended to be used for handling hard-shell capsules, which are typically made of two moulded parts, namely the body and the cap, made of gelatine or other suitable material. Such capsules are relatively fragile objects. In addition, in a typical manufacturing process, the body and the cap once moulded are telescopically pre-assembled in view of being automatically separated for filling. The capsules are designed such that the body and the cap can be separated from their pre-assembled state with a low separation force. It is therefore essential that the empty pre-assembled capsules are handled with care to avoid causing any damage or separation during transfer.

The capsule processing equipments concerned by the invention, as they are used in a context of mass production, are required to accurately and repeatedly process large numbers of capsules with high throughput. In a production line, the capsules to be processed, which are continuously fed from a manufacturing station, need to be singulated from a bulk and presented in a uniform position for processing.

The invention more specifically relates to an apparatus comprising:
- a hopper for containing a bulk of capsules, said hopper having, in a normal use position, an upper portion with an upper inlet for feeding the capsules into the hopper and a side wall; and
- a conveying belt for transferring the capsules from the hopper within the processing equipment, said conveying belt travelling in an inclined travel direction for receiving capsules from said hopper, the belt being provided with successive cavities each adapted to accommodate a single capsule.

Such an apparatus is known in the prior art, for example from U.S. Pat. No. 3,756,402. In this known apparatus, the transfer of the capsules from the hopper to the belt is achieved by relatively complex means, including rollers to suitably position the capsules and suction means to attract the capsules in respective pockets of the conveyor.

This apparatus is not adapted to the current level of throughput required to fit with the high performing manufacturing stations.

It is an object of the invention to solve the above-mentioned problem by providing a low cost apparatus for handling capsules adapted to reliably singulate capsules from a bulk and transport them in a pre-determined position, which meets the essential requirement of causing no damage to the capsules at high processing speeds.

It is a further object of the invention to provide a simple apparatus with enhanced flexibility in production, in other words easily adaptable to different size of capsules.

This is achieved by the apparatus according to the invention, which is of the above-defined type and is characterized in that the apparatus is adapted to singulate capsules in the cavities of the conveying belt from the bulk, into a pre-defined and repeatable position.

Advantageously, the apparatus of the invention may have one or more of the following optional features:
- the cavities of the belt are arranged in a transverse direction with respect to the travel direction, whereby the capsules are conveyed in the respective cavities with their axis transverse to said travel direction;
- the cavities of the belt are arranged in a single row;
- the cavities of the belt are open at both ends, whereby both ends of each capsule are accessible to respective processing devices from both sides of the belt while said capsule is conveyed on the belt;
- each cavity of the belt is defined by a concave or flat bottom surface and, respectively extending on the front side and on the rear side of the bottom surface with respect to the travel direction, a convex surface and a substantially upright surface, both connecting to the outer surface of the belt;
- the angle of the inclined direction with respect to the vertical direction is in the range of 15° to 45°, preferably in the range of 25° to 35°; and
- the belt is dismountable whereby it can be replaced to fit with different capsule dimensions.

According to the invention, there is also provided a capsule processing equipment suitable to be supplied with capsules and singulate all the supplied capsules for sequential processing, said capsule processing equipment comprising an apparatus for handling capsules as described above.

A first preferred embodiment of the capsule processing equipment of the invention consists of a capsule inspection equipment.

Advantageously, the capsule inspection equipment of the invention may comprise one or more of the following optional features:
- the equipment further comprises, arranged on both sides of the belt path downstream the hopper, two end inspection devices, each comprising illumination means and image capturing means adapted to capture an optical signal of the respective end of each capsule while conveyed on the belt;
- the equipment further comprises a system for inspecting the surface of the capsules, including one or more image capturing means;
- the system for inspecting the surface of the capsules comprises
  - a rotary carrousel arranged downstream the conveying belt, said carrousel having a rotary wheel and a plurality of circumferentially arranged spindles axially projecting from the wheel, the spindles being adapted to take the capsules from the successive cavities of the belt, by suction of one end of the capsule, and to rotate about their axis with respect to the wheel; and
  - a surface inspection device having illumination means and image capturing means adapted to capture an image of the surface of each capsule while transported on the carrousel and rotated about its axis by the respective spindle.

A second preferred embodiment of the capsule processing equipment of the invention consists of a capsule printing equipment.

Optionally, the capsule processing equipment may comprise means for rotating the capsules about their axis of a certain angle, preferably equal to 180°, while conveyed on the belt, whereby different portions of each capsule are exposed, respectively downstream and upstream said means for rotating the capsules.

Preferred embodiments of the invention will now be described in more details, by way of example only, with reference to the accompanying drawings, in which:

FIG. 1 to 5 show a first embodiment of a capsule processing equipment according to the invention under the form of a capsule inspection equipment 1, said equipment consisting of an capsule inspection equipment suitable to be integrated in a capsule production line.

Figure 1:
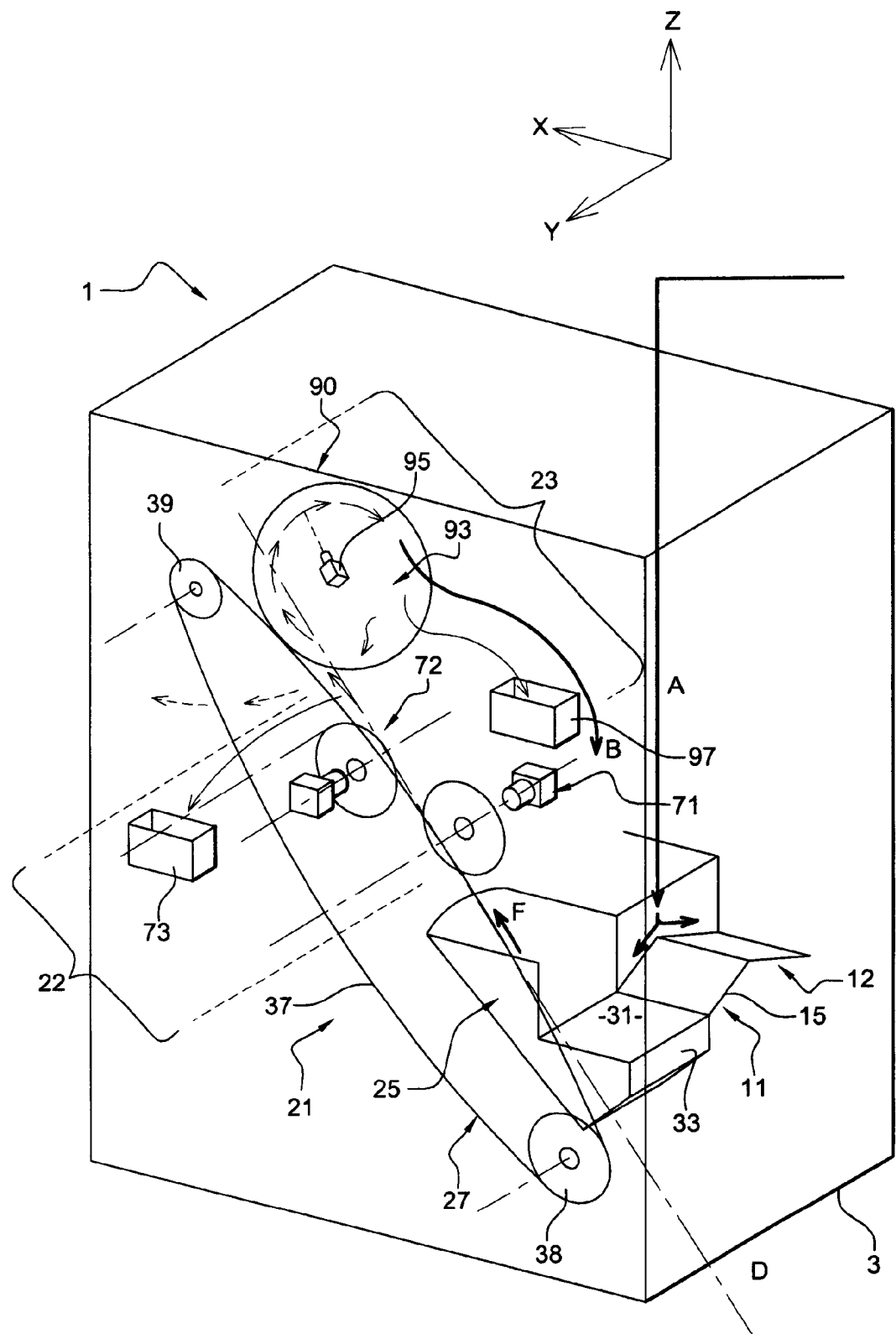
FIG. 1 is a schematic perspective view of a first embodiment of capsule inspection equipment including an apparatus for handling the capsules according to the invention.

In the represented embodiment, with particular reference to FIG. 1, a station (not shown) of the production line is arranged upstream the equipment 1 and continuously or repeatedly supplies the equipment with large numbers of capsules. The flow of capsules from the manufacturing station into the equipment 1 is represented by the arrow A.

This equipment 1 is particularly suitable to process hard capsules, which are commonly used in pharmaceutical or dietary supplement industry.

Such hard capsules are typically made in two parts—body and cap—of gelatine (in some cases of non-gelatinous material) and pre-assembled to constitute empty capsules ready for filling. The empty capsules are manufactured according to a mass production process including the following successive steps:
- a moulding step, where the bodies and caps are separately moulded;
- a drying step;
- a pre-assembling step; and
- a surface treatment step, for example a step consisting of treating the capsules by a lubricant or a surfactant.

The equipment 1 is designed to inspect 100% of the pre-assembled empty capsules fed from the upstream station and reject the capsules found to present unacceptable defects. The processing of the capsules is carried out at a high speed, which is required to be consistent with the capability of the manufacturing station.

For the sake of clarity, the orientation of FIG. 1 is given by a system of axis X, Y, Z wherein Z is a vertical axis and X, Y are horizontal axis, with Y being defined as a transversal axis. The equipment 1 is shown in its normal use position with respect to this system of axis and, in the whole description, the orientation and position terms are defined with reference to this system of axis.

On FIG. 1, the general direction of the flow of capsules is given by the arrows A and F, A representing the introduction of capsules into the equipment and F representing the general flow of capsules inside the equipment. The terms "upstream" and "downstream" in the whole description should be interpreted with reference to this general flow direction.

In the example shown, the equipment 1 has a stationary frame 3 and two identical parallel processing lines 11, 12 arranged within the frame 3 so as to be equally fed by the flow of capsules A. In order to split the incoming flow of capsules A in two equivalent sub-flows as shown on FIG. 1, the equipment is provided at the inlet thereof with a splitter 15 in the form of an upside-down V-shaped plate vertically arranged down to the flow A. Only one 11 of these processing lines will be described thereafter, the other 12 being identical and symmetrically arranged with respect to a median plane XZ of the equipment.

The processing line 11 mainly comprises
- an apparatus 21 for handling the capsules fed into the equipment 1;
- an end inspection system 22 for inspecting the ends of the capsules while handled by the handling apparatus 21 and consequently rejecting the capsules found defective;
- a surface inspection system 23 arranged downstream the handling apparatus 21 in an upper portion of the equipment, for inspecting the peripheral surface of the capsules and consequently rejecting the capsules found defective;
- an outlet represented by the outgoing flow of capsules—arrow B; and
- an electronic control unit (not shown) to automatically control the operation of the processing line.

The apparatus 21 for handling the capsules includes
- a hopper 25 fixedly attached to the frame 3 for collecting the capsules from the splitter 15 and containing the bulk capsules; and
- a belt conveyor 27 downstream the hopper 25 for singulating the capsules from the bulk contained in the hopper and transferring the capsules within the processing equipment, from the hopper to the surface inspection system 23 through the end inspection system 22.

The hopper 25 comprises, at an upper portion thereof, an inlet 31 in communication with the splitter 15 for feeding the capsules into the hopper. The hopper 25 also has a side wall 33 with a downwards converging shape. The side wall 33 is fixed with respect to the frame 3.

The belt conveyor 27 mainly comprises a conveying belt 37 and driving means 38, 39, such as wheels in mesh or friction engagement with the belt 37 for running it with a certain linear speed in a travel direction F along axis D as the wheels are rotated. The travel direction F along axis D, corresponding to the straight line between the two centres of rotation of the wheels 38, 39, is inclined with respect to the vertical direction Z. As represented, the belt 37 is in fact convexly curved, the curvature being significantly magnified on FIG. 1. This convex shape enhances the stability of the belt. The wheels 38, 39 have a transversal horizontal axis Y, the belt 37 extending and being movable in a substantially vertical plane XZ. One of the represented wheels 38, 39 may be a driving wheel whereas the other one may be a driven wheel. The belt conveyor 27 may comprise additional wheels and guides (not shown) providing supporting surfaces to the belt to ensure that the belt is maintained in the same plane with a suitable tension and at a desired inclination angle.

The conveying belt 37 is designed to be adaptable to the capsules fed into the equipment, so as to meet the requirement of making the equipment flexibly adaptable to the type of production, i.e. mainly the size of the capsules produced in the production line.

To this end, the conveying belt 37 of this embodiment is dismountable with respect to the driving means 38, 39 so as to be easily replaced.

The belt 37 is formed with cavities 43, successively arranged in a single row in the travel direction, the cavities being all identical and regularly spaced by a predetermined pitch in said travel direction. Each cavity 43 is transversally Y oriented, with respect to the travel direction, and is adapted to accommodate a single capsule 45 with its axis (typically the common axis of the cylindrical parts of the body and cap) also transversally oriented, as shown on FIG. 2. The capsules are conveyed on the belt 37 in this transverse position in the respective cavities 43.

The particular shape of the cavities 43 is adapted to present the capsules in a predetermined manner for the processing device downstream the hopper 25. In this specific embodiment, the cavities 43 are open both ends 47, with respect to the transversal axis Y, whereby both ends of each capsule (typically the domes of the body and cap) are accessible to respective end inspection devices from both sides of the belt while the capsule is conveyed on the belt 37. The width of each cavity 43, which corresponds in the example shown to the width of the belt 37, is thus substantially equal to the length of the capsules to be processed.

The transverse direction of the cavities permits a high packing density of the capsules on the belt, which is an important factor in achieving high throughput.

The particular shape of the cavities 43 is also adapted to contribute to the singulation of the capsules from the hopper 25 into the cavities and to the stabilization of the capsules in the respective cavities while conveyed on the belt 37.

It is indeed desirable that all the cavities are filled with a capsule on each pass at the hopper outlet, in order to ensure that the equipment operates at a high throughput, and that the capsule is stably positioned in the cavity so that the processing—including an image capture in the described embodiment—is accurate.

It is moreover critical that there is a single capsule in each cavity so as to make the processing of the capsule possible.

To this end, the cavities 43 roughly have a wave shape, including:
- a concave or flat bottom surface 51,
- a convex surface 53, extending from the front side of the bottom surface 51—with respect to the travel direction of the belt—to an outer surface 54 of the belt, and
- a substantially upright surface 53, extending from the rear side of the bottom surface 51 to the outer surface 54.

It will be appreciated that in the embodiment described, the capsules are positioned in the cavities of the belt in a reproducible and pre-determined manner which does not involve rectifying the capsules. The capsules are not rectified i.e. placed with the body and the cap always in the same orientation, but the capsules rather have their axis oriented in the same direction corresponding to the axis of the cavities and have their ends in the same position on this axis.

The open ends of the cavities of the belt allow the detection of the orientation cap/body by an inspection system and the subsequent adaptation of the illumination. Such a discrimination of the orientation cap/body by electronic processing can advantageously replace the physical rectification of the capsules before inspection, the physical rectification being more complex to achieve and involving more costly means.

It was found that the shape thus defined in general terms is particularly effective to meet the above cited requirements, but it will be appreciated that the specific dimensions of the cavities will be dependent on the type of capsules to be processed.

The belt 37 can be dismounted from the driving means 38, 39 (and more generally from the rest of the apparatus) and replaced, when a change occurs in the size of capsules to be processed by the equipment, by another belt fitting with these different capsule dimensions.

With reference to FIG. 1, the interaction between the hopper 25 and the belt 37 will now be explained with more details.

As illustrated on FIG. 1, the conveying belt 37 is movable along an outlet of the hopper in the same inclined direction D. The belt outer surface is thus substantially parallel to the outlet.

The outlet and the belt 37 are arranged in direct communication such that the bulk capsules contained in the hopper 25 can continuously cover a section of the belt 37 over a length corresponding to several cavities 43. In other words, provided that sufficient quantity of capsules is fed in the hopper, the apparatus 21 is designed so that a section of the belt 37 is constantly submerged by the capsules. At any moment, when the equipment 1 is operated and the belt 37 is run at a predetermined linear speed, several cavities 43 are covered by the bulk capsules. It will be appreciated that the side wall 33 is designed to constrain the capsules toward the belt 37, with no (or very limited) possibility to escape. For example, the edges of the side wall 33 should not be spaced from the outer surface 54 of the belt by more than the width of a capsule.

Figure 2:
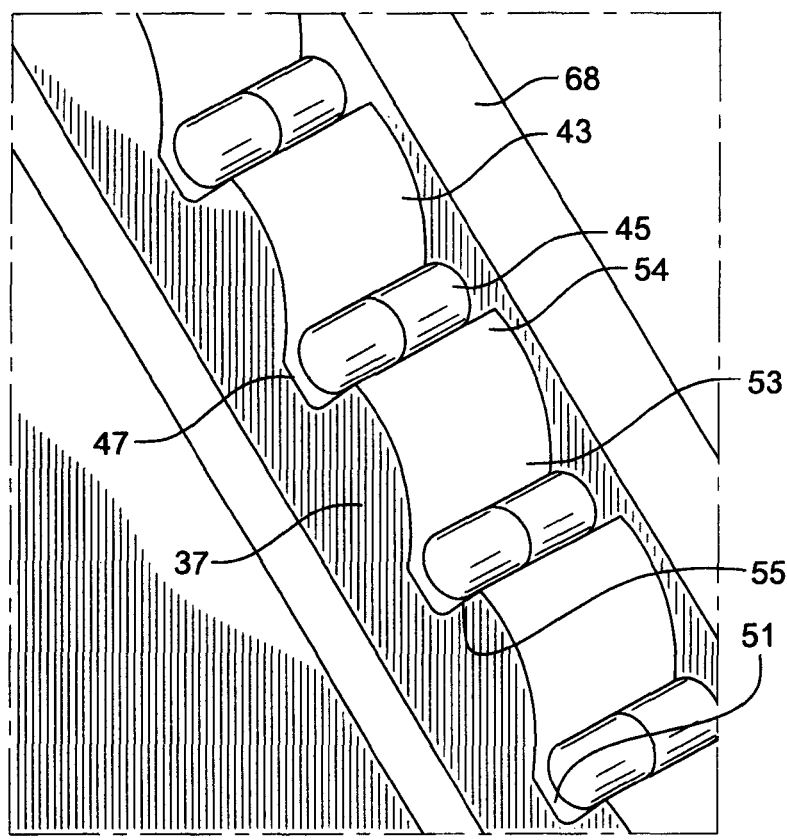
FIG. 2 is an enlarged detail view of a section of the conveying belt shown on FIG. 1, illustrating the shape of the cavities and the position of the capsules in the cavities.
Figure 3:
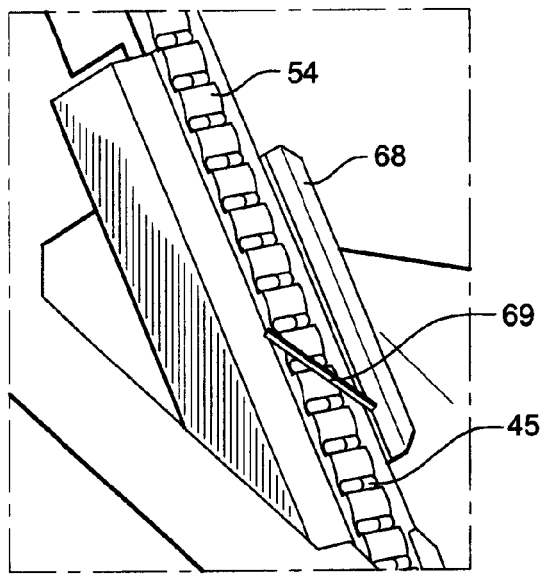
FIG. 3 is an enlarged perspective view of a detail of FIG. 1, corresponding to a lower section of the conveying belt and illustrating transfer of capsules on the conveying belt directly downstream the hopper.

Due to the interaction between the belt 37 and the hopper 25, the apparatus 21 is adapted to singulate capsules in the cavities 43 of the conveying belt 37 from the bulk, into a pre-defined and repeatable position as shown on FIG. 2, for a sequential processing of the capsules conveyed on the belt 37.

In addition to the structure of the connection between the hopper 25 and the belt 37, several parameters have a significant influence on the efficiency of the apparatus 21 in terms of throughput, ability to singulate the capsules and stability of the capsules while conveyed on the belt, such as:
- shape of the pockets 43 as previously mentioned;
- angle of inclination (D,Z);
- linear speed of the belt;
- submerged length i.e. length of the belt 37 covered by the bulk capsules from the hopper.

In this respect, the angle of inclination formed between D and Z is preferably in the range of 15° to 45°, and more preferably in the range of 25° to 35°.

The submerged length is a function of the size of the hopper and the angle of inclination. It is selected to provide good fill rate at the target machine speed without excessive hopper size and or capsule capacity. Typically, submerged length will be within the range 500 mm to 1500 mm. It is possible to reduce the hopper capacity without reducing submerged length by introducing hopper baffles.

As the case with the pocket shape, the preferred submerged length is dependent on the capsule size.

The apparatus further comprises additional means for effectively singulating capsules 45 and filling every cavity 43 on each pass, these means including for example lateral guiding members 68 and a wiper blade 69 attached to the hopper 25 and arranged immediately downstream the hopper.

The guiding members 68, in the example shown, are constituted of plates laterally arranged in close relationship with the respective lateral sides of the belt 37, which are able either to remove or put in the right position capsules laterally protruding from the respective cavities 43.

The wiper blade 69 extends across and flushes the outer surface 54 of the belt 37, in an inclined direction with respect to the travel direction D. The blade 69 is thereby able to remove misaligned or multiple capsules i.e. capsules superposed to another capsule in a cavity and/or projecting from a cavity.

Figure 4:
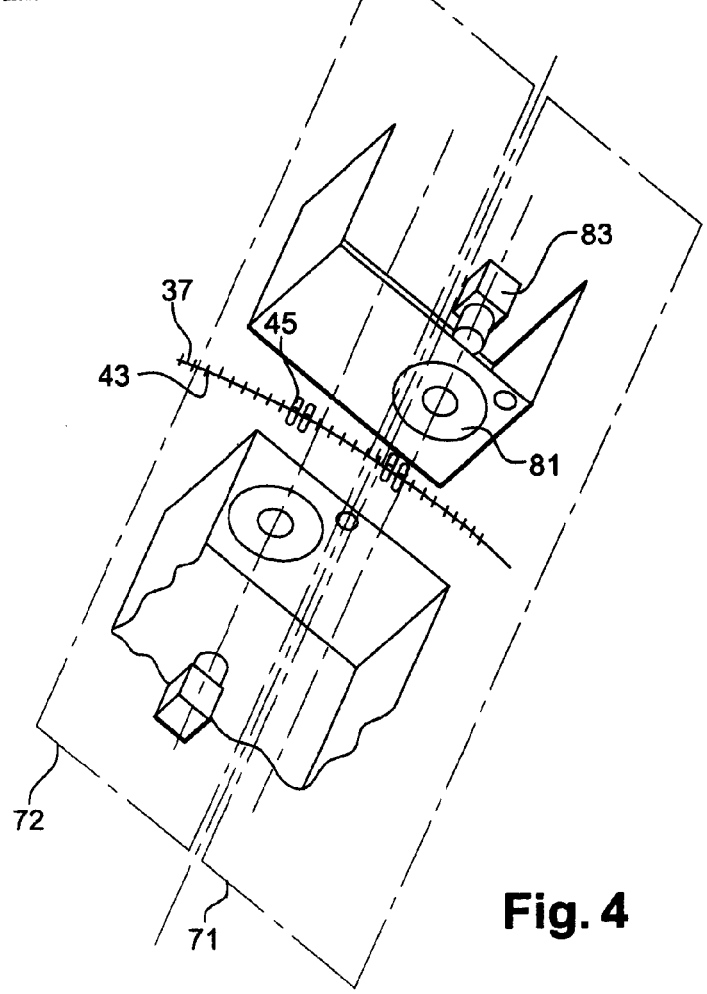
FIG. 4 is an enlarged schematic perspective view of an end inspection station of the equipment represented on FIG. 1.

Referring to FIGS. 1 and 4, the main components of the end inspection system 22 will now be briefly described.

The end inspection system 22 includes:
- two end inspection devices 71, 72 arranged on both sides of the belt path downstream the hopper 25;
- means (not shown) arranged downstream the end inspection devices 71,72 for removing defective capsules from the belt 37;
- electronic processing means (not shown) adapted to control the end inspection devices 71, 72, acquire information from the same, determine whether a given capsule inspected by the end inspection devices is defective (i.e. is found with unacceptable defects with respect to a reference) and deliver a control signal to the blowing means to remove the defective capsules; and
- a bin 73 for receiving capsules from the belt 37 which are found defective by the processing means and removed from the belt 37 by the blowing means.

Each end inspection device 71, 72 comprises illumination means 81 and a camera—more generally image capturing means—83 adapted to capture an image of the respective end of each capsule 45 while conveyed on the belt 37.

Figure 5:
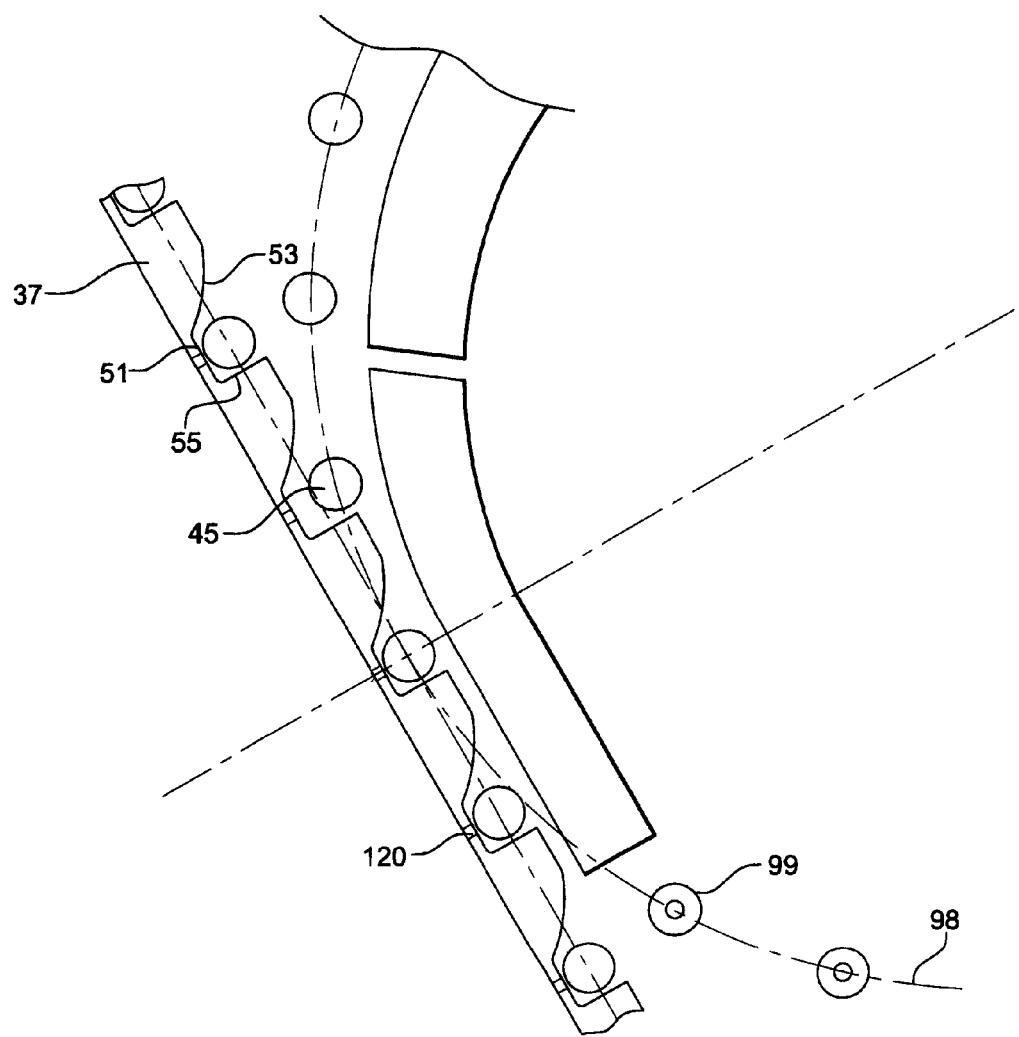
FIG. 5 is an enlarged side view of an upper part of the equipment of FIG. 1, corresponding to the capsule transfer area between the conveying belt and the carrousel of the surface inspection system.

With reference to FIGS. 1 and 5, it will be seen that the surface inspection system 23, which is provided to inspect the surface of the cylindrical portion of the capsules, comprises:
- a rotary carrousel 90 arranged downstream the conveying belt 37 adapted to take the capsules from the belt 37 and having the capsules rotated on their own axis while rotated on the carrousel;
- a surface inspection device 93 having illumination means (not shown) and image capturing means such as cameras 95 adapted to capture an image of the surface of each capsule while transported on the carrousel 90 and rotated about its axis;
- electronic processing means (not shown) adapted to acquire information from the cameras 95, build up an integral image of the surface of each capsule, determine whether a given capsule inspected by the surface inspection device 93 is defective (i.e. is found with unacceptable defects with respect to a reference) and deliver a control signal to the carrousel 90 to remove the defective capsules; and
- a bin 97 for receiving capsules from the carrousel 90 which are found defective by the electronic processing means.

As visible on FIG. 5, the carrousel 90 has a rotary wheel 98 and a plurality of circumferentially arranged spindles 99 axially Y projecting from the wheel 98. The spindles 99 are adapted to take the capsules from the successive cavities 43 of the belt 37, by suction of one end of the capsule 45, and to rotate about their axis Y with respect to the wheel 98. The transfer of the capsules from the belt to the carrousel can also be aided by an air jet. A given capsule is removed from the carrousel 90, either by actuating a mechanical rejecting gate when the capsule is found defective so that the capsule is ejected to the bin 97, or by stopping the suction when the capsule is found to be correct by the inspection system, whereby the capsule is transferred to the next station of the production line.

Figure 6:
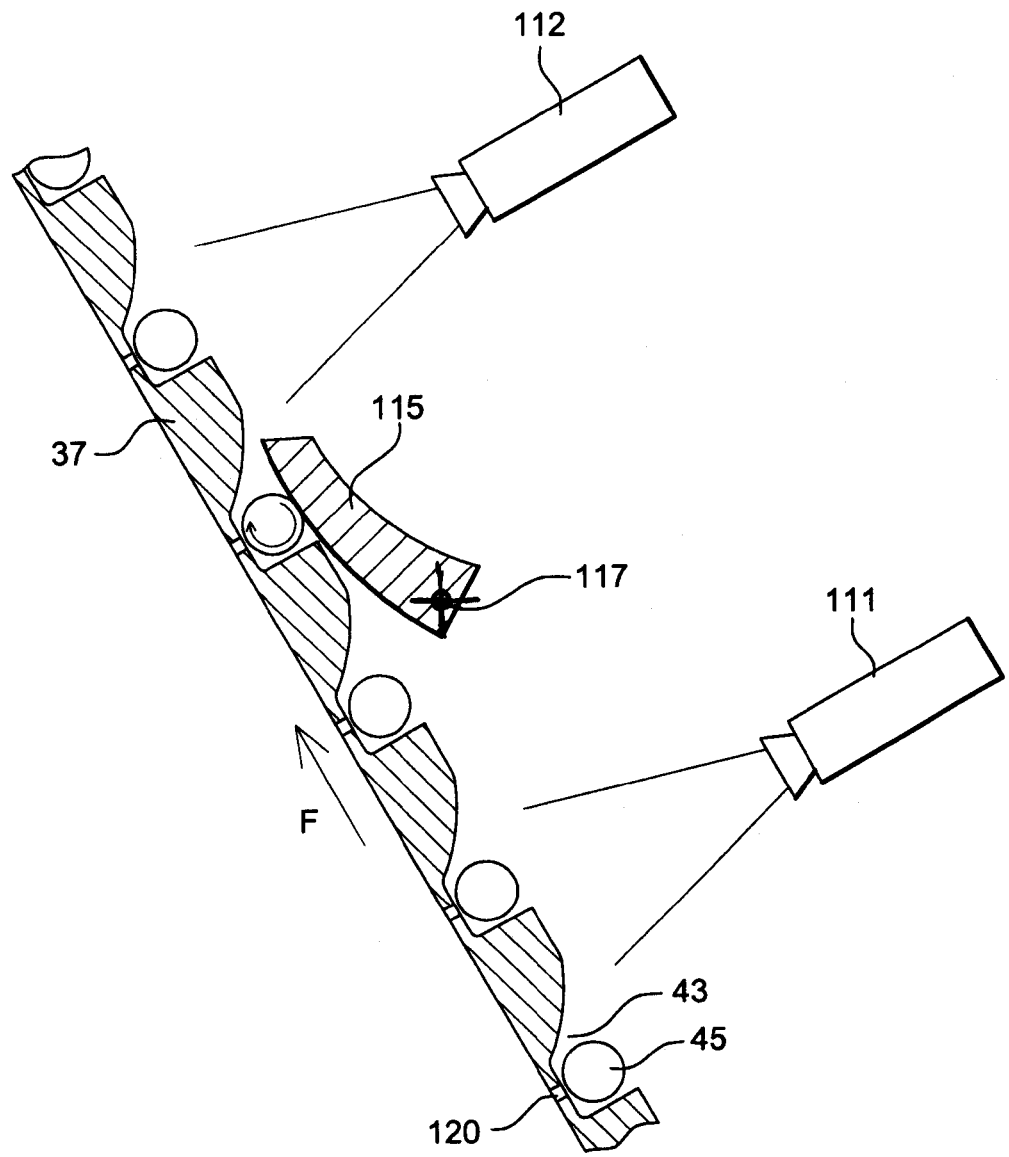
FIG. 6 is a schematic partial side view of a second embodiment of a capsule inspection equipment according to the invention.

A second embodiment of a capsule inspection equipment according to the invention is schematically illustrated on FIG. 6.

This embodiment essentially differs from the firstly described embodiment, in that the surface inspection of the capsules is achieved while the capsules 45 are conveyed on the belt 37. To this end, the equipment comprises, arranged on the path of the belt 37, an upstream camera 111 and a downstream camera 112. The cameras 111, 112 are arranged and oriented so as to be able to capture respective images of a portion of the surface of each capsule while located in a cavity 43. The two cameras 111, 112 are similarly oriented towards the outer surface of the belt 37, such that they are able to capture an image of one half of the peripheral surface of the capsule i.e. corresponding to a peripheral surface over 180°.

The equipment further comprises a friction member 115 arranged between the two cameras 111, 112 on the path of the belt 37 for rotating the capsules about their longitudinal axis in their respective cavity. The friction member 115 is formed by a flexible finger touching the outer surface of the belt 37, so as to frictionally contact the capsules and rotate them while conveyed on the belt between the two cameras 111, 112. Preferably, the friction member 115 is adapted to rotate each capsule over an angle equal to 180°, whereby the two complementary halves of the capsule peripheral surface are successively exposed respectively to the upstream camera 111 and the downstream camera 112. Other means for rotating capsules may include air jets mounted above capsules.

The friction member 115 may optionally be adjustably mounted on a fixed part of the equipment, for example about an axis 117, so as to be adjusted to the size of the capsules to be processed.

On FIGS. 5 and 6, it has been illustrated that the apparatus for handling the capsules may advantageously include additional means to position and stabilize the capsules in their respective cavities 43. These means include in the illustrated embodiment a vacuum source (not shown) and channels 120 formed in the belt 37 for a fluid communication between the vacuum source and the respective cavities 43. The fluid communication is established on a certain path where the suction effect is required to either aid attraction of the capsule in the cavity or stabilize the capsule in the cavity for an accurate inspection. The communication can then be interrupted on a subsequent path, where the capsule needs to be transferred from the belt after inspection.

The vacuum applies a small force to the capsule holding it firmly into the cavity. This gives benefits in preventing the capsule from jumping in the cavity or being lost from the cavity so improving effective fill rate and operation at higher speed.

It will be appreciated that the invention provides an apparatus able to carefully handle capsules at a high speed and to transfer the capsules in a precise and repeatable position for presentation to a processing system. The invention makes it possible to integrate the associated processing equipment in a production line without reducing the throughput achieved by the upstream manufacturing stations, in particular by the moulding station.

The invention claimed is:

1. An apparatus for handling capsules in a capsule processing equipment, comprising
   a hopper for containing a bulk of capsules, said hopper having, in a normal use position, an upper portion with an upper inlet for feeding the capsules into the hopper and a side wall; and
   a conveying belt for transferring the capsules from the hopper within the processing equipment, said conveying belt travelling in an inclined travel direction for receiving capsules from said hopper, the belt being provided with successive cavities each adapted to accommodate a single capsule, wherein the apparatus is adapted to singulate capsules in the cavities of the conveying belt from the bulk, into a pre-defined and repeatable position, wherein the cavities of the belt are open at both ends, whereby both ends of each capsule are accessible to respective processing devices from both sides of the belt while said capsule is conveyed on the belt, and wherein the cavities of the belt are arranged in a transverse direction with respect to the travel direction, whereby the capsules are conveyed in the respective cavities with their axis transverse to said travel direction.

2. The apparatus according to claim 1, wherein the cavities of the belt are arranged in a single row.

3. The apparatus according to claim 1, wherein each cavity of the belt is defined by a concave or flat bottom surface and, respectively extending on the front side and on the rear side of the bottom surface with respect to the travel direction, a convex surface and a substantially upright surface, both connecting to the outer surface of the belt.

4. The apparatus according to claim 1, wherein the angle of the inclined direction with respect to the vertical direction is in the range of 15° to 45°.

5. The apparatus according to claim 4, wherein the angle of the inclined direction with respect to the vertical direction is in the range of 25° to 35°.

6. The apparatus according to claim 1, wherein the belt is dismountable whereby the belt can be replaced to fit with different capsule dimensions.

7. Capsule processing equipment suitable to be supplied with capsules and singulate all the supplied capsules for sequential processing, wherein said capsule processing equipment comprises an apparatus for handling capsules according to claim 1.

8. The capsule processing equipment according to claim 7, wherein said capsule processing equipment consists of a capsule inspection equipment.

9. The capsule processing equipment according to claim 8, wherein the cavities of the belt are arranged in a single row, and wherein the capsule processing equipment comprises, arranged on both sides of the belt path downstream the hopper, two end inspection devices, each comprising illumination means and image capturing means adapted to capture an optical signal of the respective end of each capsule while conveyed on the belt.

10. The capsule processing equipment according to claim 7, wherein said capsule processing equipment further comprises means for rotating the capsules about their axis to a certain angle, while conveyed on the belt, whereby different portions of each capsule are exposed, respectively downstream and upstream said means for rotating the capsules.

11. The capsule processing equipment according to claim 10, wherein the angle is equal to 180°.

12. The capsule processing equipment claim according to 8, wherein said capsule processing equipment further comprises a system for inspecting the surface of the capsules, including one or more image capturing means.

13. The capsule processing equipment according to claim 12, wherein said system for inspecting the surface of the capsules comprises:

a rotary carrousel arranged downstream the conveying belt, said carrousel having a rotary wheel and a plurality of circumferentially arranged spindles axially projecting from the wheel, the spindles being adapted to take the capsules from the successive cavities of the belt, by suction of one end of the capsule, and to rotate each capsule about its axis with respect to the wheel; and a surface inspection device having illumination means and image capturing means adapted to capture an image of the surface of each capsule while each capsule is transported on the carrousel and rotated about its axis by the respective spindle.

14. The capsule processing equipment according to claim 7, wherein said capsule processing equipment consists of a capsule printing equipment.

* * * * *

UNITED STATES PATENT AND TRADEMARK OFFICE
CERTIFICATE OF CORRECTION

PATENT NO. : 8,646,591 B2
APPLICATION NO. : 13/130322
DATED : February 11, 2014
INVENTOR(S) : Thomas Marcelina Louis De Ruijter et al.

It is certified that error appears in the above-identified patent and that said Letters Patent is hereby corrected as shown below:

In the Claims

Claim 12, col. 10, lines 17-18, "claim according to 8" should read -- according to claim 8 --.

Signed and Sealed this
Twentieth Day of May, 2014

Michelle K. Lee
*Deputy Director of the United States Patent and Trademark Office*